United States Patent
Whitman et al.

(10) Patent No.: US 9,427,220 B2
(45) Date of Patent: Aug. 30, 2016

(54) TISSUE REPAIR IMPLANT AND DELIVERY DEVICE AND METHOD

(71) Applicant: MICRO INTERVENTIONAL DEVICES, INC, New Hope, PA (US)

(72) Inventors: Michael P. Whitman, New Hope, PA (US); Peter Datcuk, Quakertown, PA (US)

(73) Assignee: MICRO INTERVENTIONAL DEVICES, INC., New Hope, PA (US)

( * ) Notice: Subject to any disclaimer, the term of this patent is extended or adjusted under 35 U.S.C. 154(b) by 0 days.

(21) Appl. No.: 13/828,256

(22) Filed: Mar. 14, 2013

(65) Prior Publication Data

US 2013/0211426 A1    Aug. 15, 2013

Related U.S. Application Data

(62) Division of application No. 13/010,766, filed on Jan. 20, 2011.

(60) Provisional application No. 61/296,898, filed on Jan. 21, 2010.

(51) Int. Cl.
*A61B 17/10* (2006.01)
*A61B 17/00* (2006.01)
(Continued)

(52) U.S. Cl.
CPC ....... *A61B 17/0057* (2013.01); *A61B 17/0401* (2013.01); *A61B 17/10* (2013.01); *A61B 2017/00575* (2013.01); *A61B 2017/00579* (2013.01); *A61B 2017/00632* (2013.01);
(Continued)

(58) Field of Classification Search
CPC ................ A61B 2017/00579; A61B 17/0057; A61B 17/0401; A61B 17/08; A61B 17/10; A61B 2017/0057; A61B 2017/00575; A61B 2017/00623; A61B 2017/0401; A61B 2017/0409; A61B 2017/0412; A61B 2017/0427; A61B 2017/0437; A61B 2017/044; A61B 2017/0464; A61B 2017/064; A61B 2017/0647; A61B 2017/0648
See application file for complete search history.

(56) References Cited

U.S. PATENT DOCUMENTS 3,897,035 A    7/1975    Solo
3,959,960 A    6/1976    Santos
(Continued)

FOREIGN PATENT DOCUMENTS

EP    0 790 038    8/1997
EP    1 595 504    11/2005
(Continued)

OTHER PUBLICATIONS

Merriam-Webster Dictionary, Definition of "reel", http://www.merriam-webster.com/dictionary/reel as accessed on Apr. 23, 2016.*
International Search Report and Written Opinion, dated Mar. 11, 2011, issued in corresponding International Application No. PCT/US2011/021946.
International Search Report and Written Opinion, dated Apr. 8, 2011, issued in corresponding International Application No. PCT/US2011/021952.
(Continued)

*Primary Examiner* — Todd J Scherbel
(74) *Attorney, Agent, or Firm* — Kenyon & Kenyon LLP

(57) ABSTRACT

A device for the repair of tissue and methods of use and manufacturing thereof are described herein. Applications for the use of the device include, e.g., repair of atrial septal defects (ASD), patent foramen ovale (PFO), left atrial appendage closure and stent graft fixation among other applications throughout the anatomy. The implant portion of the device is available in a variety of sizes and configurations to accommodate the vast complexity of the target anatomy.

29 Claims, 9 Drawing Sheets

(51) Int. Cl.
*A61B 17/064* (2006.01)
*A61B 17/04* (2006.01)
(52) U.S. Cl.
CPC *A61B2017/0408* (2013.01); *A61B 2017/0412* (2013.01); *A61B 2017/0427* (2013.01); *A61B 2017/0435* (2013.01); *A61B 2017/0437* (2013.01); *A61B 2017/0464* (2013.01); *A61B 2017/0647* (2013.01); *A61B 2017/0648* (2013.01)

(56) References Cited

U.S. PATENT DOCUMENTS

| | | | |
|---|---|---|---|
| 4,204,541 A | | 5/1980 | Kapitanov |
| 4,488,523 A | | 12/1984 | Shichman |
| 4,669,473 A | | 6/1987 | Richards et al. |
| 4,741,330 A | | 5/1988 | Hayhurst |
| 4,873,976 A | * | 10/1989 | Schreiber ............ 606/213 |
| 4,884,572 A | | 12/1989 | Bays et al. |
| 4,968,315 A | | 11/1990 | Gatturna |
| 4,969,892 A | | 11/1990 | Burton et al. |
| 4,978,265 A | | 12/1990 | De Wan |
| 5,059,206 A | * | 10/1991 | Winters ............ 606/213 |
| 5,127,412 A | | 7/1992 | Cosmetto et al. |
| 5,356,424 A | | 10/1994 | Buzerak et al. |
| 5,370,661 A | | 12/1994 | Branch |
| 5,372,146 A | * | 12/1994 | Branch ............ 128/898 |
| 5,478,353 A | * | 12/1995 | Yoon ............ 606/213 |
| 5,505,735 A | * | 4/1996 | Li ............ 623/13.14 |
| 5,562,704 A | | 10/1996 | Tamminmaki et al. |
| 5,569,264 A | * | 10/1996 | Tamminmaki et al. ...... 606/104 |
| 5,584,859 A | | 12/1996 | Brotz |
| 5,601,557 A | | 2/1997 | Hayhurst |
| 5,694,782 A | | 12/1997 | Alsenz |
| 5,782,844 A | | 7/1998 | Yoon et al. |
| 5,792,142 A | | 8/1998 | Galitzer |
| 5,814,051 A | | 9/1998 | Wenstrom, Jr. |
| 5,860,991 A | | 1/1999 | Klein et al. |
| 5,964,782 A | | 10/1999 | Lafontaine et al. |
| 5,976,127 A | | 11/1999 | Lax |
| 5,976,139 A | | 11/1999 | Bramlet |
| 5,993,475 A | | 11/1999 | Lin et al. |
| 6,010,525 A | | 1/2000 | Bonutti et al. |
| 6,027,523 A | * | 2/2000 | Schmieding ............ 606/232 |
| 6,030,410 A | | 2/2000 | Zurbrugg |
| 6,120,525 A | | 9/2000 | Westcott |
| 6,159,234 A | | 12/2000 | Bonutti et al. |
| 6,174,323 B1 | | 1/2001 | Biggs et al. |
| 6,231,561 B1 | | 5/2001 | Frazier et al. |
| 6,231,592 B1 | | 5/2001 | Bonutti et al. |
| 6,331,182 B1 | | 12/2001 | Tiefenbrun et al. |
| 6,387,113 B1 | | 5/2002 | Hawkins et al. |
| 6,468,293 B2 | | 10/2002 | Bonutti et al. |
| 6,500,184 B1 | | 12/2002 | Chan et al. |
| 6,569,187 B1 | | 5/2003 | Bonutti et al. |
| 6,663,633 B1 | | 12/2003 | Pierson, III |
| 6,692,499 B2 | | 2/2004 | Tormala et al. |
| 6,884,251 B2 | | 4/2005 | Spence et al. |
| 6,966,916 B2 | | 11/2005 | Kumar |
| 7,037,315 B2 | | 5/2006 | Sancoff et al. |
| 7,087,073 B2 | | 8/2006 | Bonutti |
| 7,104,949 B2 | | 9/2006 | Anderson et al. |
| 7,147,652 B2 | | 12/2006 | Bonutti et al. |
| 7,166,127 B2 | | 1/2007 | Spence et al. |
| 7,195,634 B2 | * | 3/2007 | Schmieding et al. ...... 606/326 |
| 7,220,265 B2 | | 5/2007 | Chanduszko et al. |
| 7,235,090 B2 | | 6/2007 | Buckman et al. |
| 7,361,185 B2 | | 4/2008 | O'Malley et al. |
| 7,390,329 B2 | | 6/2008 | Westra et al. |
| 7,416,554 B2 | | 8/2008 | Lam et al. |
| 7,569,062 B1 | | 8/2009 | Kuehn et al. |
| 7,651,509 B2 | | 1/2010 | Bojarski et al. |
| 7,736,378 B2 | | 6/2010 | Maahs et al. |
| 7,780,701 B1 | | 8/2010 | Meridew et al. |
| 7,780,702 B2 | | 8/2010 | Shiono |
| 7,833,238 B2 | | 11/2010 | Nakao |
| 7,850,712 B2 | | 12/2010 | Conlon et al. |
| 8,070,802 B2 | | 12/2011 | Lamphere et al. |
| 8,241,227 B2 | | 8/2012 | Ohnishi et al. |
| 8,337,525 B2 | | 12/2012 | Stone et al. |
| 8,361,113 B2 | | 1/2013 | Stone et al. |
| 8,366,766 B2 | | 2/2013 | Berreklouw |
| 8,382,776 B2 | | 2/2013 | Ducharme |
| 8,425,539 B2 | | 4/2013 | Binmoeller et al. |
| 2003/0074021 A1 | | 4/2003 | Morriss et al. |
| 2003/0078604 A1 | | 4/2003 | Walshe |
| 2003/0078671 A1 | | 4/2003 | Lesniak et al. |
| 2003/0092969 A1 | | 5/2003 | O'Malley et al. |
| 2003/0093117 A1 | | 5/2003 | Saadat |
| 2003/0097148 A1 | | 5/2003 | Valimaa et al. |
| 2004/0087981 A1 | | 5/2004 | Berube et al. |
| 2004/0138707 A1 | | 7/2004 | Greenhalgh |
| 2004/0220596 A1 | | 11/2004 | Frazier et al. |
| 2004/0220610 A1 | | 11/2004 | Kreidler et al. |
| 2005/0021057 A1 | | 1/2005 | St. Goar et al. |
| 2005/0038449 A1 | | 2/2005 | Sancoff et al. |
| 2005/0055027 A1 | | 3/2005 | Yeung et al. |
| 2005/0075654 A1 | | 4/2005 | Kelleher |
| 2005/0125011 A1 | | 6/2005 | Spence et al. |
| 2005/0177180 A1 | | 8/2005 | Kaganov et al. |
| 2005/0187568 A1 | | 8/2005 | Klenk et al. |
| 2005/0222665 A1 | | 10/2005 | Aranyi |
| 2005/0228413 A1 | | 10/2005 | Binmoeller et al. |
| 2005/0234508 A1 | | 10/2005 | Cummins et al. |
| 2005/0251175 A1 | | 11/2005 | Weisenburgh et al. |
| 2005/0256532 A1 | | 11/2005 | Nayak et al. |
| 2005/0283189 A1 | | 12/2005 | Rosenblatt |
| 2006/0004364 A1 | | 1/2006 | Green et al. |
| 2006/0030884 A1 | | 2/2006 | Yeung et al. |
| 2006/0190042 A1 | | 8/2006 | Stone et al. |
| 2006/0235413 A1 | | 10/2006 | Denham et al. |
| 2006/0247644 A1 | * | 11/2006 | Bhatnagar et al. ............ 606/75 |
| 2006/0282088 A1 | | 12/2006 | Ryan |
| 2006/0287661 A1 | | 12/2006 | Bolduc et al. |
| 2007/0016286 A1 | | 1/2007 | Herrmann et al. |
| 2007/0073320 A1 | | 3/2007 | Mikkaichi et al. |
| 2007/0112425 A1 | | 5/2007 | Schaller et al. |
| 2007/0142837 A1 | | 6/2007 | Dreyfuss |
| 2007/0185530 A1 | | 8/2007 | Chin-Chen et al. |
| 2007/0203511 A1 | | 8/2007 | Vardi |
| 2008/0027477 A1 | | 1/2008 | Obermiller et al. |
| 2008/0051837 A1 | | 2/2008 | To et al. |
| 2008/0132948 A1 | | 6/2008 | Surti et al. |
| 2008/0161850 A1 | | 7/2008 | Weisenburgh et al. |
| 2008/0228193 A1 | | 9/2008 | Matityahu |
| 2008/0300547 A1 | | 12/2008 | Bakos |
| 2008/0300629 A1 | | 12/2008 | Surti |
| 2009/0005800 A1 | | 1/2009 | Franer et al. |
| 2009/0012560 A1 | | 1/2009 | Hunter et al. |
| 2009/0024163 A1 | | 1/2009 | Zeiner et al. |
| 2009/0082790 A1 | | 3/2009 | Shad et al. |
| 2009/0198107 A1 | | 8/2009 | Park et al. |
| 2009/0216264 A1 | | 8/2009 | Friedman et al. |
| 2009/0228040 A1 | | 9/2009 | Mas et al. |
| 2009/0236401 A1 | | 9/2009 | Cole et al. |
| 2009/0240264 A1 | | 9/2009 | Tuval et al. |
| 2009/0248067 A1 | | 10/2009 | Maiorino |
| 2009/0275960 A1 | | 11/2009 | Provenza et al. |
| 2009/0287245 A1 | | 11/2009 | Ostrovsky et al. |
| 2009/0287304 A1 | | 11/2009 | Dahlgren et al. |
| 2010/0010457 A1 | | 1/2010 | Ewers et al. |
| 2010/0016885 A1 | * | 1/2010 | Eidenschink et al. ...... 606/213 |
| 2010/0049213 A1 | * | 2/2010 | Serina et al. ............ 606/139 |
| 2010/0049289 A1 | | 2/2010 | Lund et al. |
| 2010/0087854 A1 | | 4/2010 | Stopek et al. |
| 2010/0094341 A1 | | 4/2010 | Raju |
| 2011/0028995 A1 | | 2/2011 | Miraki et al. |
| 2011/0054539 A1 | | 3/2011 | Knopfle et al. |
| 2011/0178534 A1 | | 7/2011 | Whitman et al. |
| 2011/0178535 A1 | | 7/2011 | Whitman |
| 2011/0178537 A1 | | 7/2011 | Whitman |
| 2011/0190811 A1 | | 8/2011 | Shanley |
| 2011/0288583 A1 | | 11/2011 | Goraltchouk et al. |
| 2012/0022586 A1 | | 1/2012 | Whitman et al. |

(56) References Cited

U.S. PATENT DOCUMENTS

| | | |
|---|---|---|
| 2012/0059395 A1 | 3/2012 | Kehdy et al. |
| 2012/0116418 A1 | 5/2012 | Belson et al. |
| 2012/0245634 A1 | 9/2012 | Kaplan |
| 2012/0296345 A1 | 11/2012 | Wack et al. |
| 2013/0211426 A1 | 8/2013 | Whitman et al. |
| 2013/0211450 A1 | 8/2013 | Whitman |

FOREIGN PATENT DOCUMENTS

| | | |
|---|---|---|
| WO | 93/14705 | 8/1993 |
| WO | 01/85035 | 11/2001 |
| WO | 03/059173 | 7/2003 |
| WO | 2005/004727 | 1/2005 |
| WO | 2005/058239 | 6/2005 |
| WO | 2007/098212 | 8/2007 |
| WO | WO-2008/045635 A2 | 4/2008 |
| WO | 2008/067384 | 6/2008 |
| WO | 2008/116203 | 9/2008 |

OTHER PUBLICATIONS

International Search Report and Written Opinion, dated Jun. 1, 2011, issued in corresponding International Application No. PCT/US2011/021949.

International Search Report and Written Opinion, dated Mar. 23, 2011, issued in corresponding International Application No. PCT/US2011/021947.

European Supplementary Search Report, dated Jun. 13, 2013, issued in corresponding European Patent Application No. 11735202.1.

International Search Report and Written Opinion, dated Sep. 8, 2014, issued in corresponding International Application No. PCT/US2014/30868.

International Search Report and Written Opinion, dated Nov. 23, 2015, issued in International Application No. PCT/US2015/035191.

Extended European Search Report issued in European Patent Application No. 11735204.7, dated Sep. 2, 2015.

International Search Report and Written Opinion issued in PCT/US2015/035427, dated Sep. 16, 2015.

\* cited by examiner

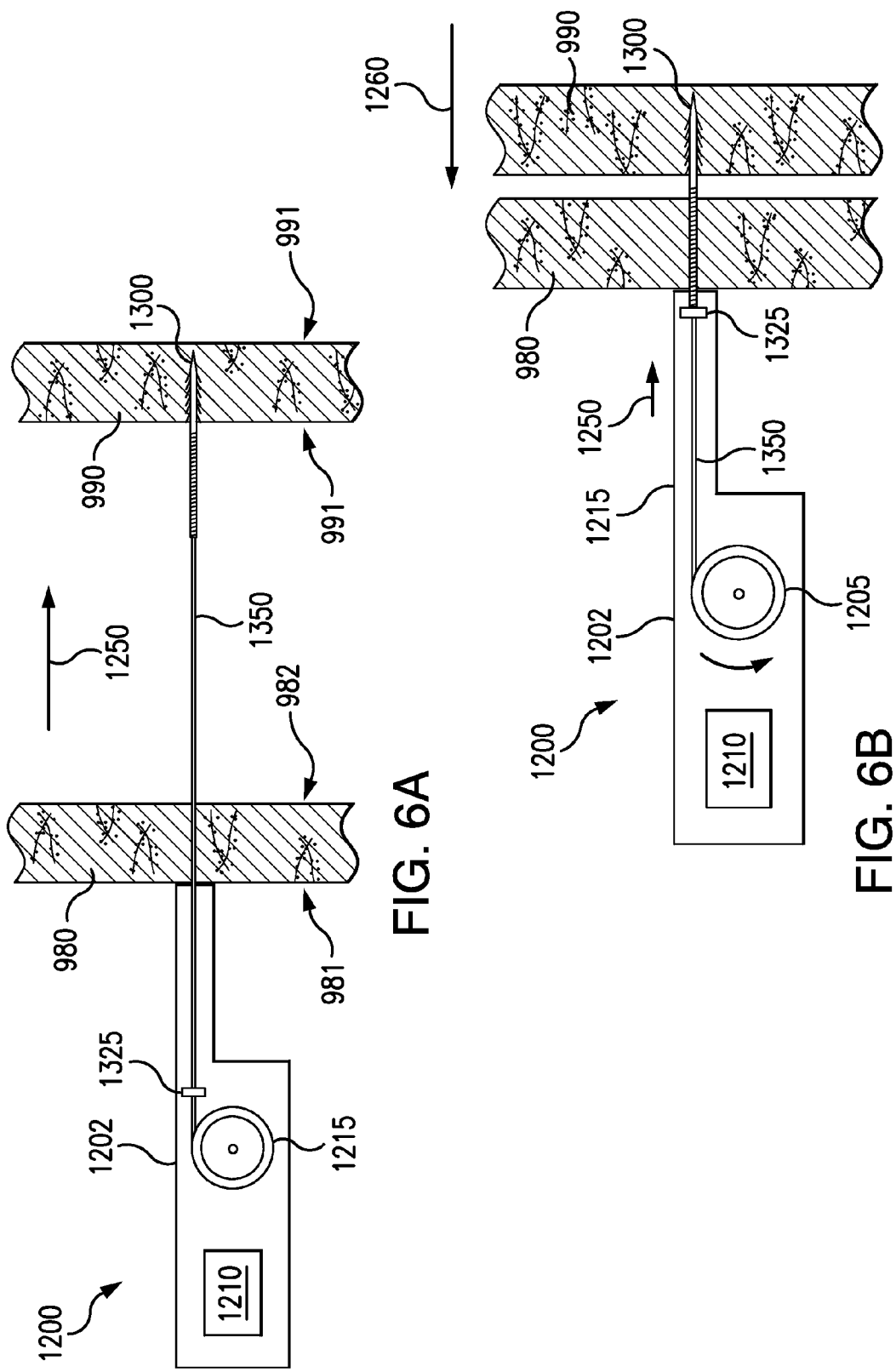

TISSUE REPAIR IMPLANT AND DELIVERY DEVICE AND METHOD

CROSS-REFERENCE TO RELATED APPLICATIONS

This application is a divisional of and claims the benefit of the filing date of U.S. patent application Ser. No. 13/010,766, filed Jan. 20, 2011, which claims the benefit of U.S. Provisional Patent Application Ser. No. 61/296,868, filed on Jan. 20, 2010, each of which is expressly incorporated herein in its entirety by reference thereto.

Further, each of the following is hereby incorporated in its entirety by reference thereto: U.S. patent application Ser. No. 13/010,777, filed on Jan. 20, 2011, U.S. patent application Ser. No. 13/010,774, filed on Jan. 20, 2011; and U.S. patent application Ser. No. 13/010,769, filed on Jan. 20, 2011.

FIELD OF THE INVENTION

The present invention relates to a tissue repair implant and delivery device and method.

BACKGROUND INFORMATION

Some surgical interventions require the repair of tissue, e.g., closure of the tissue or graft fixation. These procedures may include, for example, treatment of atrial septal defects (ASD), patent foramen ovale (PFO), left atrial appendage closure, stent graft fixation, and hernia repair, among others.

ASDs and PFOs are considered to be two of the leading contributors to embolic stroke. Stroke is the third leading cause of death in the United States and one of the leading causes of adult disability. It is estimated that 80% of strokes are preventable and that repair of existing ASDs and PFOs will reduce the incidence. When ASDs and PFOs are present in the heart, a debilitating condition may occur. Deoxygenated blood may pass from the right atrium through either the ASD and/or PFO into the oxygenated blood of the left atrium. It has been estimated that approximately one in four individuals in the general population have a PFO. Individuals who have unknown causes of stroke (cryptogenic stroke), have a 40 percent increase in the likelihood of a PFO being present. PFO is even more prevalent in individuals who have had strokes under that age of 55.

U.S. Pat. No. 7,220,265 describes a device for closure of PFO, wherein a catheter is directed into proximity of the PFO. The catheter is inserted between the septum primum and the septum secundum into the left atrium. The catheter then deploys a first closure member, e.g., a "grappling hook element," in the left atrium. The catheter is then drawn back into the right atrium where a second closure member, e.g., a second grappling hook element, is deployed. The first and second closure members are connected by a central connecting member such that the septal tissues are compressed together between the two opposed closure members. U.S. Pat. No. 7,220,265 also discloses a method of closing the PFO using sutures, whereby implantable anchors purportedly limit the need for a continuous thread. The devices and methods of U.S. Pat. No. 7,220,265 require maneuvering of a medical device, e.g., a catheter or suture needle, in both the right and left atria. This may present substantial complexity and difficulty to the procedure, possibly increasing the likelihood of surgeon error and/or increasing the time required to complete the procedure.

Further, typical existing anchors are configured to joining soft tissue to hard tissue, since there is no way to take out the slack with soft tissue to soft tissue joining.

Thus, there is a need for a closure mechanism and method that is simple to operate and only requires access to one side of the tissue or tissues. Further, there is a need for a reliable closure that may be precisely located.

Moreover, some tissue defects, e.g., some heart defects and inguinal hernias, require the implantation of a mesh. In the example of an inguinal hernia, the mesh is intended to create a barrier against abdominal cavity contents protruding through a defect the abdominal peritoneum and inguinal canal. A known treatment for such hernias involves applying a single anchor to a mesh, e.g., a square mesh, then pulling the mesh taut and applying a second anchor to the mesh. This sequential fastening and tightening is repeated until the mesh is secured over the defect. This method is procedurally costly and time consuming, however, and there is a risk that the mesh may not be properly or sufficiently tautened, which could render the mesh ineffective in preventing the protrusion of the abdominal cavity contents through the inguinal canal.

Thus, there is also need for an implanting mechanism and method that allows for a quick and reliable securement of a mesh to repair a tissue defect, e.g., allowing for simultaneous application of fasteners.

Further, there is a need for a mechanism and method that reduces procedural costs and allows access to difficult-to-reach locations of the anatomy.

SUMMARY

According to example embodiments of the present invention, a device for the repair of tissue and methods of use and manufacturing of the device are provided. Applications for the use of the device include, e.g., repair of atrial septal defects (ASD), patent foramen ovale (PFO), left atrial appendage closure, stent graft fixation, and hernia repair, among other applications throughout the anatomy. The implant portion of the device may be provided in a variety of sizes and configurations to accommodate the vast complexity of the target anatomy.

Example embodiments of the present invention provide for an implant and a delivery device which may be used to bring adjacent tissues into approximation in order to provide a wide array of therapeutic treatments, including, e.g., repair of ASD, PFO, left atrial appendage occlusion, and stent graft fixation among many other applications in the human body, or, e.g., any suitable mammalian body.

According to example embodiments of the present invention, a fastener having a distal end and a proximal end includes an elongated body having a distal tip, and anchoring filaments extending radially outwardly from the elongated body in a proximal direction of the elongated body, the anchoring filaments configured to resist proximal movement of the elongated body when the fastener is driven in a distal direction into one or more layers of tissue.

The fastener may also have a proximal head disposed proximally from the anchoring filaments, wherein the proximal head extends radially outwardly from the elongated body and is configured to limit the depth to which the fastener is proximally driven into one or more layers of tissue.

The proximal head may be fixed to the elongated body.

The proximal head and the elongated body may be formed together as a single monolithic piece.

The fastener may further include a proximal head configured to engage a proximal portion of the elongated body.

The proximal head may include threads that engage corresponding threads on the proximal portion of the elongated body when the proximal head engages the proximal portion of the elongated body, wherein rotation of the proximal head with respect to the threads of the proximal portion of the elongated body causes movement of the proximal head along the longitudinal axis of the elongated body.

The proximal head and the elongated body together form a ratchet when the proximal head engages the proximal portion of the elongated body, wherein the proximal head is moveable distally along the elongated body and restrained from proximal movement along the elongated body.

The fastener may be formed partially or entirely of, e.g., a bio-absorbable material.

The distal tip may be tapered. The distal tip may be blunt or taper to a sharp point. The distal tip may be a cutting tip. The distal tip may include at least one concave tapered cutting edge. The distal tip may include three concave tapered cutting edges. The three concave tapered cutting edges may be equidistant from each other around a circumference of the fastener. The distal tip may be a reverse-cutting tip.

According to example embodiments of the present invention, a surgical device for implanting a fastener having proximally directed anchoring filaments includes a device body and a fastener driver coupled to the device body and configured to penetrate a first soft tissue, engaging an unsupported second soft tissue, and anchoring the fastener in the second soft tissue so that the fastener can bring the second soft tissue in direct apposition to the first soft tissue.

The fasteners are preferably driven at a speed greater than 50 meters per second, more preferably in a range of 50 to 350 meters per second, and most preferably at 350 meters per second. However, it should be understood that the fasteners may be driven at any suitable speed sufficient for the fasteners to puncture tissue.

The fastener driver may be configured to drive the fastener at a predetermined distance and velocity based on a determined distance between the first tissue and the second tissue. The fastener driver is adjustable to drive the fastener at different distances and velocities based on the determined distances between the first tissue and the second tissue. The fastener driver may be configured to impart a momentum to the fastener sufficient to drive the fastener through the first soft tissue and into the second soft tissue. The fastener driver may be configured to transfer hydraulic force to the fastener to impart the momentum. Saline may be provided for the hydraulic propulsion.

The surgical device may further include the fastener, wherein the anchoring filaments of the fastener are configured to resist proximal movement of the fastener when the fastener is driven through the first soft tissue and into the second soft tissue.

The fastener may include a proximal head and the fastener driver includes a plurality of flanges configured to contact a distal face of the proximal head to limit the depth to which the fastener is driven by the fastener driver.

The flanges may be radially expandable from each other to release the proximal head of the fastener.

The fastener may be attached to a suture.

According to example embodiments of the present invention, a surgical device comprises a fastener including an elongated body having a proximal end and a distal tip, and a filament secured to the fastener and extending from the proximal end of the elongated body.

The filament may be a braided filament.

The device may be formed by coextrusion of the fastener over the filament.

The fastener may further include anchoring filaments proximally extending from the elongated body, the anchoring filaments configured to resist proximal movement of the elongated body when the fastener is driven in a distal direction into one or more layers of tissue. The fastener and the filament may be comprised of a bio-absorbable material.

The distal tip of the fastener may be blunt. The distal tip of the fastener may taper to a sharp point. The distal tip may be tapered. The distal tip may be a cutting tip. The distal tip may include at least one concave tapered cutting edge. The distal tip may include three concave tapered cutting edges. The three concave tapered cutting edges may be equidistant from each other around a circumference of the fastener.

The distal tip may be a reverse-cutting tip.

According to example embodiments of the present invention, a surgical device comprises a fastener including a proximal end and a distal tip, the fastener configured to anchor into a tissue when distally driven into the tissue, a filament secured to the fastener and extending from the proximal end of the elongated body, and a fastener driver coupled to the device body and configured to distally drive the fastener into the tissue.

The filament may be a braided filament.

The distance to which the fastener is driven may be limited by a predetermined amount of slack in the filament prior to the driving, the distance being limited by the tautening of the filament.

The fastener may include proximally extending anchoring filaments configured to anchor the fastener into the tissue. The fastener driver may be configured to drive the fastener into through a first tissue and into a second tissue such that the fastener anchors in the second tissue. The first and second tissues may be soft tissues, the fastener driver being configured to impart a momentum to the fastener sufficient to drive the fastener through the first soft tissue and into the second soft tissue when the second soft tissue is unsupported. The fastener driver may be configured to drive the fastener at a predetermined distance and velocity based on a determined distance between the first tissue and the second tissue. The fastener driver may be adjustable to drive the fastener at different distances and velocities based on the determined distances between the first tissue and the second tissue. The fastener driver may be configured to drive the fastener using a hydraulic propulsion. Saline may be provided for the hydraulic propulsion.

The surgical device may further comprise a capstan configured to proximally reel the filament after the fastener has been driven by the fastener driver.

The proximal reeling of the filament may cause a corresponding proximal movement of the tissue when the fastener is anchored in the tissue.

The fastener may be molded to the filament. The fastener may be coextruded with the filament. The filament may be a braided filament. The fastener may include a plurality of molded radially disposed anchoring filaments.

According to example embodiments of the present invention, a surgical device comprises an elongated fastener body, and wings disposed on a distal portion of the fastener body, wherein the body has external corrugations and the wings have external corrugations.

According to example embodiments of the present invention, a method of purposefully bringing two adjacent tissues together includes, the placement of a delivery system device in approximation of the tissue, creating surface tension with the device, and ejecting an absorbable or non-absorbable implant from the device. The device controls the exact placement of the implant, which penetrates both tissues thus creating contact between the two tissue surfaces so that the two tissues are in approximation.

According to example embodiments of the present invention, an absorbable or non-absorbable implant has a needle-like tip tapering to a body portion that contains filaments protruded therefrom, the filaments present over a percentage of the length of the body. The implant may transition from the portion with filaments to a threaded section for, e.g., the remaining percentage of the length of the body. The threaded section is capable of receiving a nut and/or head which can move independently from the body of the implant. The head is able to be independently rotated so that the head can compress the two previously penetrated adjacent tissues to bring them into apposition.

According to example embodiments of the present invention, a device includes a housing and a firing pin disposed in the housing and axially movable in the housing. The device also includes a spring coupled to the housing and the firing pin to apply a spring force between the housing the firing pin. The housing includes a distal portion configured to receive an implant. The device includes at least one of a cable and a shaft, the at least one of a cable and shaft being configured to releasably attach to a proximal end of the firing pin and to pull the firing pin to a proximal position, thereby increasing a force exerted between the spring and the housing. The at least one of a cable and a shaft is configured to release the firing pin from the proximal position to allow the firing pin to move distally forward in response to the spring force. The distal motion of the firing pin causes the firing pin to extend into the distal portion of the housing.

The device may include two or more implants in an end-to-end arrangement.

The device may be configured to cause only the distal-most of the two or more implants to be ejected when the firing pin extends into the distal portion after being released by the at least one of a cable and a shaft.

The device may include a sleeve disposed in the housing, the sleeve configured to move the firing pin and spring to a second, more distal location within the housing in order to drive the next of the two or more implants.

According to example embodiments of the present invention, an implant driving device includes a housing and a driving shaft disposed in the housing and axially movable and rotatable in the housing. The housing includes a distal portion that houses two or more implants in an end-to-end arrangement, the two or more implants being drivable by the axial movement and rotation of the driving shaft.

The proximal-most of the two or more implants may have a recess that mates with a corresponding projection of the driving shaft.

Each of the two or more fasteners may have distal end portions having a geometry that mates with a proximal recess of each of the other of the two or more fasteners.

Two or more, e.g., all, of the fasteners may be driven simultaneously, or substantially simultaneously.

The fasteners may be driven in a plurality of sets, each set of anchors being driven simultaneously, or substantially simultaneously.

Further features and aspects of example embodiments of the present invention are described in more detail below with reference to the appended Figures.

BRIEF DESCRIPTION OF THE DRAWINGS

FIGS. 6A to 6C schematically and sequentially illustrate the bringing into apposition of two tissues using a surgical implant.

DETAILED DESCRIPTION

Figure 1:
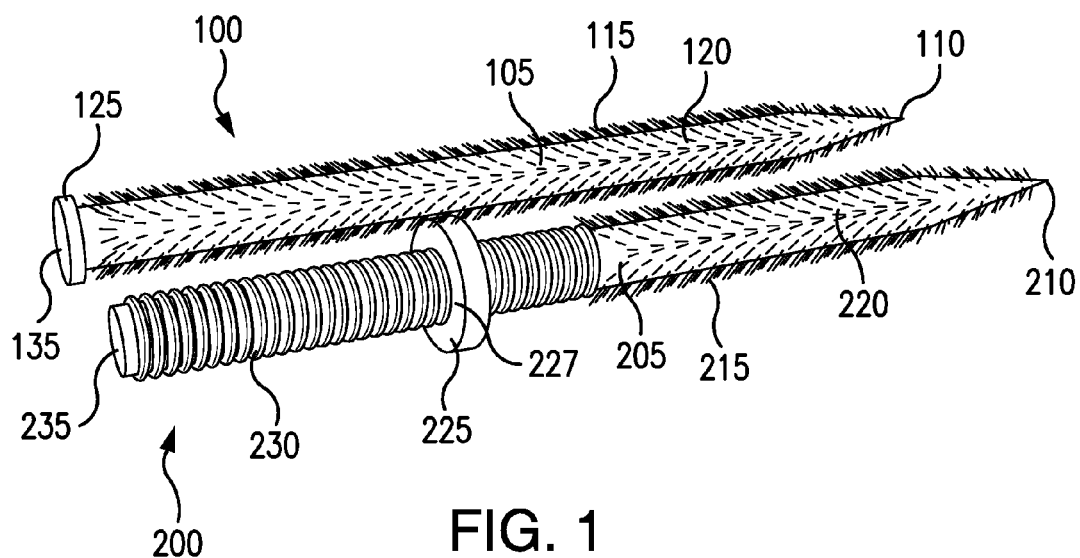
FIG. 1 is an illustration of two surgical implants.

FIG. 1 is an illustration of two surgical micro implants or fasteners 100 and 200. The surgical implants 100 and 200, which may be absorbable or non-absorbable, are designed to penetrate and join two adjacent viscera or tissue planes. The implants 100 and 200 are designed to pass through the first tissue and the second tissue under controlled rapid deployment. The implant is shaped similarly to a needle with a predetermined geometry. Each implant 100, 200 has an elongated body 105, 205 that tapers in a distal region to a needle-like tip 110, 210. Each implant 100, 200 may be deployed, as described in greater detail below, by being pushed from a precisely placed hollow needle or tube containing the implant 100, 200. The implants disclosed herein may be formed using e.g., micromachining techniques.

The micro implants 100 and 200, as well as any other implants disclosed herein may have a diameter of one millimeter, or approximately one millimeter, and a length that is in a range from 5 millimeters to 10 millimeters. According to some example embodiments, the diameter is less than one millimeter. According to some example embodiments, the diameter is in a range from 0.8 millimeters to 1.2 millimeters. It should be understood, however, that other dimensions may be provided.

The body 105, 205 of each implant 100, 200 has specifically designed micro anchoring filaments 115, 215 which arise from a core 120, 220 of the implant 100, 200 to extend outwardly from the core 120, 220. The anchoring filaments 115, 215 are located around the circumference and along at least a portion of the length of the body 105, 205 of the implant 100, 200. This allows the implant to resist removal once it has penetrated the tissue.

The filaments 115, 215, or any other filaments described herein may have any suitable dimensions. For example, it may be advantageous to provide a filament tip (i.e., free end) diameter of 0.1 millimeters and tapering toward a diameter of 0.25 millimeters at the body.

The core 120, 220 has a constant diameter along a substantial length of the body 105, 205 of the implant 100, 200. For example, the core 120 of the implant 100 has a constant cross-section, and constant diameter, from a head portion 125 to a substantially conically shaped tapered portion toward the tip 110. It should be understood however, that the implants 100 and 200 may have a more continuous taper and/or have a constant or non-constant rate of taper.

The anchoring filaments 115, 215 extend outwardly at an angle with respect to the longitudinal axis of the implant 100, 200. In this regard, the filaments, in addition to extending outwardly away from the longitudinal axis, also extend in a proximal direction, away from the tip 110, 210. This allows for the filaments 115, 215 to slide along the pierced tissue during distal driving or insertion. However, proximal movement of the implants 100, 200 from the inserted position is prevented or resisted by engagement of the outer, free ends of the filaments 115, 215 with the relatively soft tissue. The filaments 115, 215 may be flexible or substantially rigid. The filaments 115, 215 should, however, have sufficient stiffness or strength to resist proximal withdrawal of the implant 100, 200 from the inserted position. Further, although the filaments 115, 215 are illustrated as being straight, it should be understood that some or all of the filaments 115, 215 may be at least partially curved, and/or have one or more bends between straight portions and/or curved portions. Moreover, the filaments 115, 215 of a given implant 100, 200 may have constant or differing lengths, radial extensions, and/or angles with respect to the longitudinal axis of the implant 100, 200.

The filaments 115, 215, or any other anchoring filaments described herein may be provided with any appropriate density and relative spacing, depending on the particular application. For a given application, a greater density (i.e., a greater number of filaments per unit of surface area) of smaller filaments may be provided, or a lesser density of larger filaments (optionally reinforced with a shape memory alloy, e.g., nitinol and/or spring-loaded steel), while presenting the same or comparable suture retention or "pull through strength." The optional reinforcement could be a "V" shaped portion formed of shape memory alloy, e.g., nitinol and/or spring-loaded steel. The filaments 115, 215 may be absorbable or non-absorbable in whole or in part.

Each implant 100, 200 includes a proximal head 125, 225. The head 125, 225 extends radially beyond the core 120, 220 and has a larger axial cross section than the core 120, 220. The head 125, 225 may prevent the implant 100 from being driven too deeply into, or entirely through, the tissue. As the implant 100, 200 is driven distally along its longitudinal axis, the core 120, 220 pierces into and progresses through the tissue. The head 125, 225, having a larger diameter or cross section, prevents or resists the proximal portion of the implant 100, 200 from extending into the tissue. Thus, where two layers of tissue are pierced and joined, the distal layer of tissue is constrained against distal movement away from the proximal layer of tissue by engagement of the distal layer with the filaments 115, 215, and the proximal layer is constrained against proximal movement away from the distal layer by engagement of the proximal layer (e.g., the outer proximal surface of the proximal layer) with the head 125, 225.

The implant 100 differs from the implant 200 in that the implant 100 has anchoring filaments 115 provided from the tip region to an axially fixed, proximal head 125, whereas the implant 200 has a predetermined length that is externally threaded with micro threads 230 to allow the head 225, which has corresponding internal threads, to rotate about the implant, thus bringing the two adjacent tissues into approximation. In this regard, the implant 200 may be initially driven into the tissue, the distance to which is driven being limited by, e.g., friction between the implant 200 and the tissue. After the initial driving, the head 225 may be rotated, e.g., in a clockwise direction, to move the head or nut 225 distally along the longitudinal axis of the implant 200. The rotation may be performed by a rotatable driver having projections configured to engage driving recesses 227 of the head 225, as described in greater detail below. Although the head 225 has four evenly spaced recesses 227, it should be understood that any appropriate number of recesses 227 may be provided. Further, the micro tightening nut or head 225 may have projections as an alternative or in addition to the recesses, the projections engageable by the driver to rotate the head 225. Moreover, any other appropriate driving mechanism may be provided. For example, the driver may grip the outer surface of the head 225 to impart rotation via friction, or the radially outwardly facing surface of the head 225 may have one or more flat surfaces engageable by the driver.

Contact between the distal face of the head 225 and the proximal surface of the proximal layer of tissue would in turn cause the proximal layer of tissue to move toward the distal layer of tissue, which is axially constrained by the filaments 215. The head 225 may be prevented from rotating in the opposition direction by friction between the threads or any appropriate locking or securing mechanism, e.g., detents. During the tightening rotation of the head 225, the body 205 may be prevented from rotating by the engagement of the filaments 215 with the tissue or any other appropriate mechanism.

Each implant 100, 200 has a proximal surface 135, 235 via which a driving force may be applied. The proximal surface 135 of the implant 100 corresponds to the proximal surface of the proximal head 125, while the proximal surface 235 of the implant 200 has a smaller diameter, which is the same or substantially the same as the diameter of the core 220.

Although the implants 100, 200 have cores 120, 220 and heads 125, 225 with circular cross sections, it should be understood that other cross-sections may be provided, e.g., rectangular, triangular, oval, polygonal, and/or any other regular or irregular shape. Further, it should be understood that the anchoring filaments 115, 215 may be evenly spaced apart or may have non-uniform spacing. Moreover, the filament density, i.e., the number of the filaments 115, 215 per unit of surface area of the core 120, 220 may be constant, or may vary.

Modern manufacturing processes allow for near nano technology applications. This allows the implants 100, 200 to be manufactured in a size and complexity that may not have been possible in years past. The implant 100, 200 may be injection molded of either absorbable or non absorbable polymers and then processed to add the features of the protruding filaments 115, 215 and the threaded features 227. The head 225 of the implant 200 is manufactured separately and to the same or similar tolerances so that the interface between the implant threads 230 and the head 225 of the implant 200 will thread precisely upon one another.

Although the implants 100 and 200 are formed of polymer, it should be appreciated that any appropriate material may used, e.g., metal or a composite material.

The materials and methods of manufacturing the implants 100 and 200 are applicable to any of the implants described herein.

In order to accurately penetrate adjacent tissues that are not held or secured on a distal side, a rapid penetration of each layer of tissue may be required in order to affect penetration of both tissue layers. If an implant 100, 200 is applied slowly, the tissue may be pushed distally away by the implant and/or needle without adequate penetration. Thus, some example delivery mechanisms eject the implant a relatively high velocity. In some preferred examples, saline is used to pressurize the channel within the catheter or needle at such a rate that the plunger will eject the implant at the precise velocity. Other example embodiments utilize a spring-loaded mechanical mechanism to eject the implant. Further example embodiments push the implant using long push rods which run the length of the catheter. The ejection modality is computer-controlled. However, it should be understood that the ejection may be, e.g., operator-controlled. For example, the ejection force may be predetermined and repeatable by a mechanical system, e.g., a spring-loaded system, which is triggered by an operator, e.g., a surgeon.

Figure 2A:
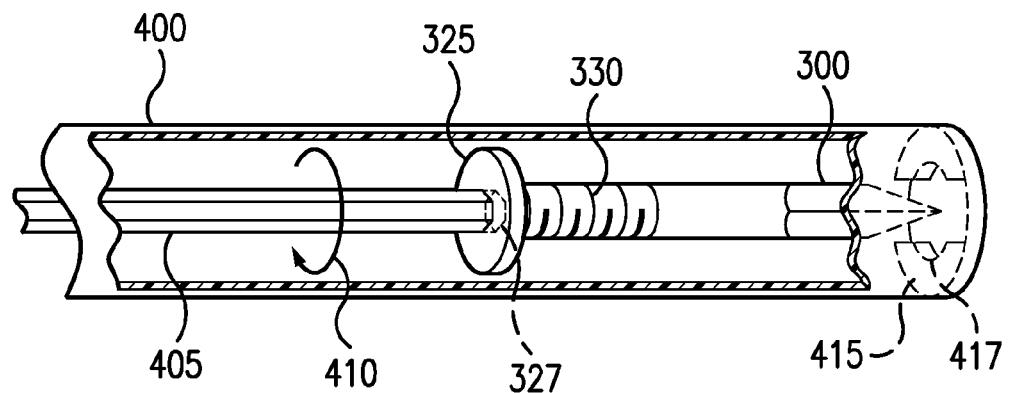
FIGS. 2A and 2B are schematic illustrations of surgical implants with driving mechanisms.
Figure 2B:
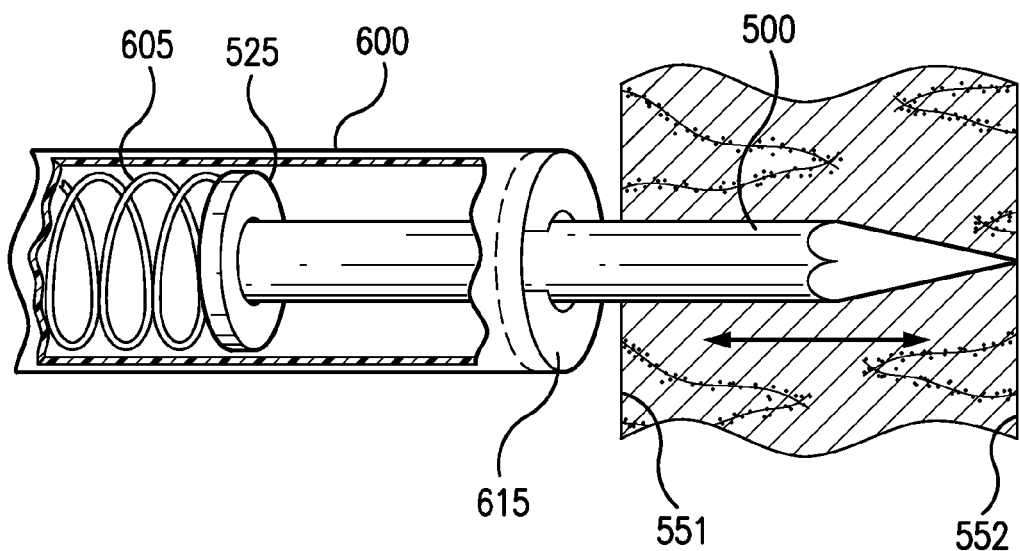

FIGS. 2A and 2B are schematic illustrations of surgical implants 300 and 500 with driving mechanisms including catheters or needles 400 and 600.

Referring to FIG. 2A, implant 300 shares many features in common with implants 100 and 200. Implant 300 differs, however, in that it includes reverse threads 330 and a proximal head 325 having a driving recess 327. The driving recess has a geometry that corresponds to a rotatable driver 405 of the catheter 400, such that the driver 405 is insertable into the recess 327 to impart axial rotation to the implant 300. In this regard, rotation of the driver in a first direction 410 causes the driver to rotate in the direction 410. Although the direction 410 is clockwise (when view from a proximal location), it should be appreciated that the driver may be configured to rotate the implant 300 in the counter-clockwise direction, e.g., where the threading is reversed. The driver is configured to progressively move distally along its axis during driving to correspond to a distance which the implant is driven. The corresponding geometry of the driver 405 and the recess 327 may be selected to have any appropriate cross section, e.g., rectangular or hexagonal.

The catheter has, at a distal end portion, a pair of retention tabs 415. The retention tabs 415 have inner diameters that are less than the diameter of the proximal head 325 but greater than the diameter of the other, more distal portions of the implant 300. Thus, the retention tabs allow the distal portions of the implant 300 to be driven beyond the distal end of the catheter and into tissue, but retains the head 325 within the catheter. After the driving of the implant 300, the retention tabs may be actuated radially outwardly away from each other to allow the release of the head of the implant 300 and withdrawal of the catheter 400 away from the implant site.

Referring to FIG. 2B, the catheter 600 shares many features in common with the catheter 400, including, e.g., retention tabs 615, but differs in that it includes a spring driver 605. The spring driver 605 imparts a spring force onto the proximal head 525 of the implant 500 to impart a rapid movement from an initial proximal position to an extended distal position. The spring driver 605 may have an initial preloaded position that is not in contact with the implant 500. Thus, the spring and/or a driver portion driven by the spring may build momentum prior to engaging the implant 500. This may be suitable for imparting a more aggressive acceleration to the implant 500. When the implant is able to achieve a high speed quickly, it is able to pierce a proximal face 551 of the tissue and penetrate across the thickness of the tissue to the distal face 552, rather than simply compressing the outer proximal surface 551 of the tissue. This may be particularly suitable in allowing a system that does not require any initial structure on the back side of the tissue during the driving process.

Figure 3:
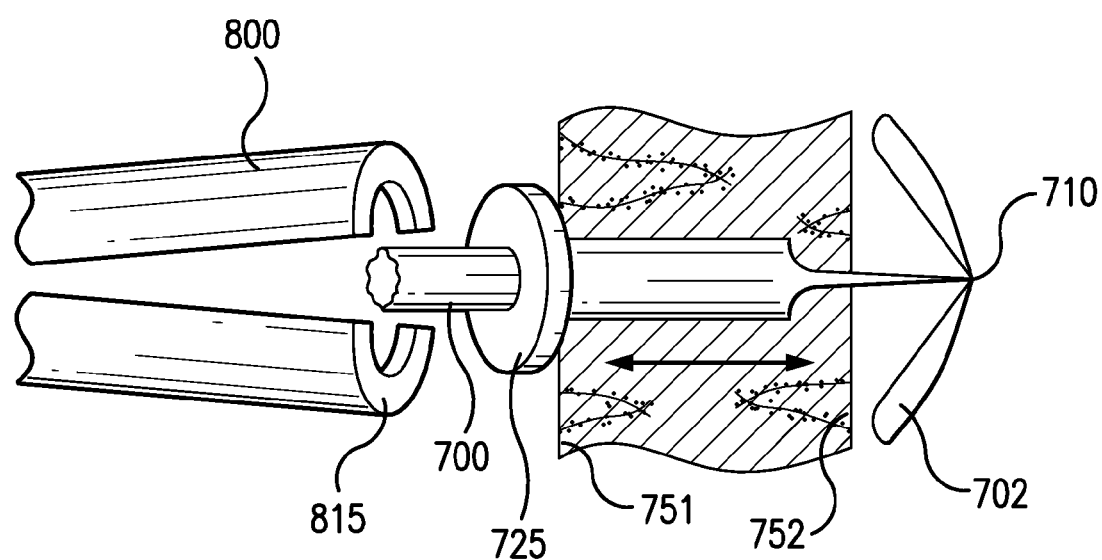
FIG. 3 is a schematic illustration of a surgical implant with a driving mechanism.

FIG. 3 is a schematic illustration of a surgical implant 700 with a driving mechanism. The driving mechanism is a catheter 800 sharing features with the catheters 400 and 600 described above, including, e.g., retention tabs 815, which are shown in their opened, or radially extended position, thereby allowing distal axial passage therethrough of the head 725 of the implant 700.

The implant 700 includes many features in common with the implants 100, 200, 300, and 500 described above, but differs in that it includes a plurality of spring loaded tabs 702, which may be formed, e.g., of a shape memory alloy, e.g., nitinol or spring-loaded steel. The spring-loaded tabs are maintained in their closed, or radially inward, position when the proximal free ends of the tabs 702 are axially disposed in the catheter 800 (in its closed position) and in the tissue through which the tabs are driven after piercing of the tissue, including a proximal face 751, by the needle-like tip 710. However, when the proximal ends of the spring loaded tabs 702 clear the distal side 752 of the tissue, the tabs are no longer radially constrained by the tissue and are able to spring radially outwardly into their open position. In the open position, the implant 700 is prevented or constrained from being proximally withdrawn through the tissue via contact between the extended tabs 702 and the distal surface 752 of the tissue. The nut or head 725 of the implant 700 may then be rotated and distally advanced as described above with regard to the head 225 of the implant 200 in order to bring the layers of tissue together.

The driver may be configured to drive the any of the fasteners described herein to a predetermined depth. The precision of the depth may be accomplished by any appropriate mechanism, e.g., a precise hydraulic driving force, engagement with flanges or other similary stops, or a filament/suture that tautens to limit the depth. Further the depth may be monitored using fluoroscopy or any other appropriate imaging mechanism. The driving mechanism may include pressurized saline or other hydraulic fluid that is pressurized through the endoscopic catheter shaft. Thus, very precise control may be accomplished.

Figure 4:
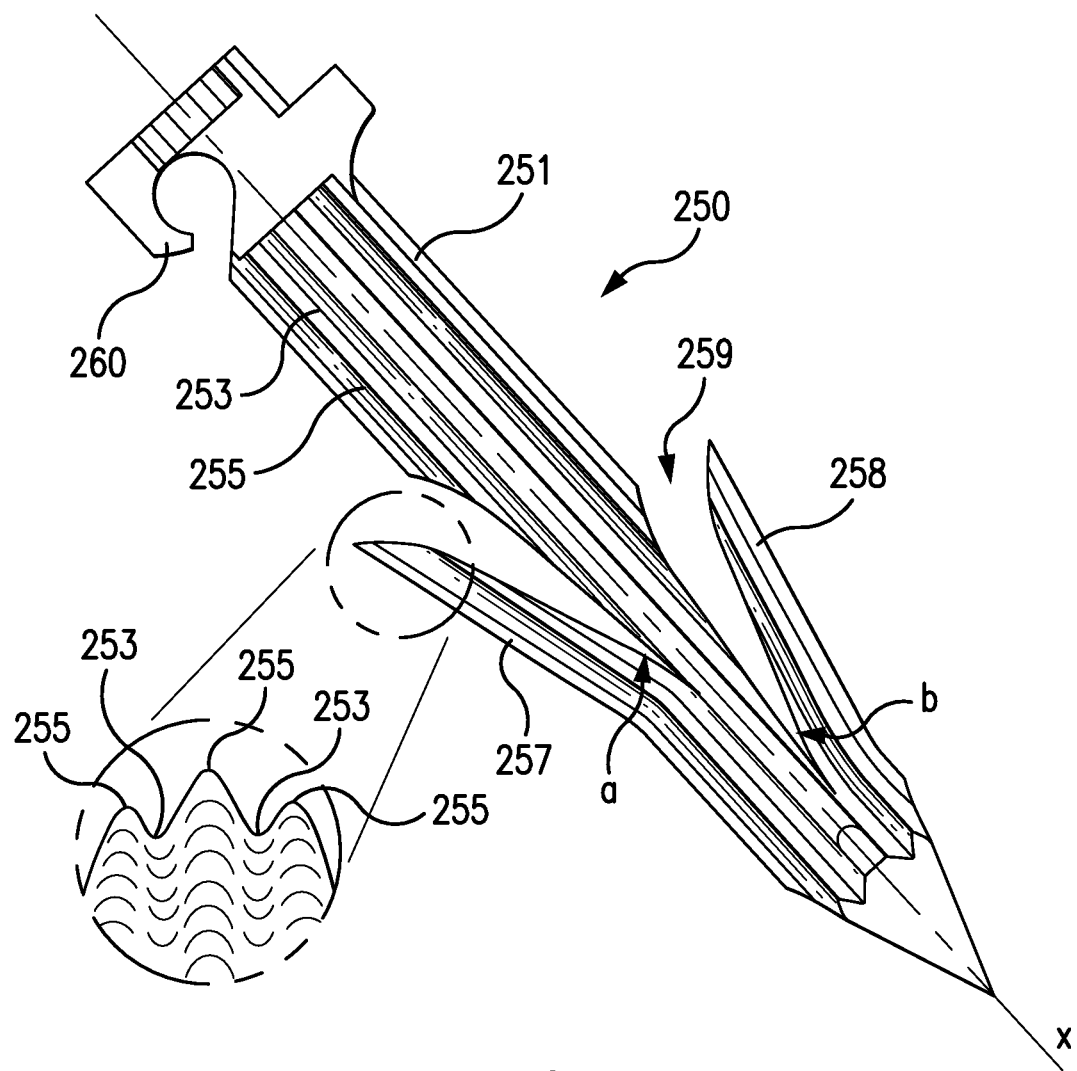
FIG. 4 is an illustration of a surgical implant.

FIG. 4 shows a fastener or implant 250. The fastener 250 includes features in common with the other fasteners disclosed herein and may be used in conjunction with any of the other fastening applications described herein. However, the fastener 250 includes a corrugated body 251. The body 251 includes grooves 253 that extend axially along the length of the body 251. Thus, extending circumferentially around the body 251, a plurality of grooves 253 alternate with a plurality of ridges 255. Further, the fastener body 251 includes a pair of split portions or clevises 257 and 258. The split portions are formed by respective splits or cuts 259 into the body 251. In this regard, the splits 259 may be formed by making a cut radially into the body 251 and extending in an axial direction. Thus, the two split portions 257 and 258 are attached to the remainder of the body 251 at a distal position and extend proximally to free ends. The free ends include a plurality of sharp protrusions along a curved surface. These points are formed due to the corrugations. In particular, the ridges 255 form the sharp protrusions, as illustrated in the inset partial side view in FIG. 4, which are advantageous for gripping tissue and preventing distal sliding of the fastener 250. Although each split portion 257 and 258 includes three such protrusions as illustrated, it should be understood that the fastener 250 may be designed such that one or more of the split portions has any other number of protrusions, including a single sharp protrusion. For example, if a larger number of sharp protrusions are desired, the body 251 could be more densely corrugated (i.e., a greater number of alternating grooves 253 and ridges 255 could be provided) and/or the angle of the cut or slice could be adjusted. Further, the length of proximal extension of the projections may be adjusted by varying the depth of the grooves 253 with respect to the ridges 255.

The split portions 257 and 258 do not substantially impede distal insertion into tissue but resist proximal movement from an insertion location by engaging the tissue. It has been discovered that the combination of the pointed and/or sharp-edged proximal ends of the split portions 257 and 258 with the alternating ridges on the proximal end of the split portions creates improved performance.

Further, the split portions or wings 257 and 258 are axially offset from each other. For example, split 257 is axially located at position a along axis x and split 258 is axially located at position b along axis x. This allows for greater structural strength of the other portions of the body 251 as compared to a non-offset configuration. In particular, since the cuts progress continually radially inward as they progress distally, a non-offset portion would have a substantially smaller amount of material in cross-section in the distal end of the cut. This would lead to a mechanically weak point or region along the axis of the body and could lead to mechanical failure, especially in fasteners of small dimensions.

The distal tip of the fastener 250 is pyramidal, with a sharp point, and a plurality of surfaces separated by edges that converge at the sharp point. Although four planar surfaces are provided, it should be appreciated that any appropriate suitable number of surfaces may be provided and that one or more or all of the surfaces may be non-planar.

The fastener 250 also includes a hooked end portion 260. The hooked portion may be suitable for coupling any other temporary and/or permanent implant.

The fastener 250 may be produced by first forming the body 251 with the corrugations, e.g., by injection molding or extrusion, and subsequently forming clevises 257 and 258, e.g., by cutting radially into the side of the body 251. As illustrated, the cut is curved, with an angle (at the proximal entry point), relative to the longitudinal axis of the body 251, that gradually decreases from the proximal initial cutting location toward the distal end of the fastener 250 and eventually becoming linear. Although the split or cut of the illustrated example is made with a curved or varying angle with respect to the longitudinal axis of the body 251, it should be understood that any appropriate cut, including a linear cut, may be made.

Although the fastener 250 includes two wings or split portions spaced equally around the radial periphery of the body 251, it should be appreciated that any number of clevises, including a single clevis may be provided and at any appropriate spacing around the radial periphery.

Furthermore, it should be understood that the corrugated split-bodied configuration may be employed in combination with any of the other fastener features disclosed herein. For example, the fastener 250 may have a split corrugated distal portion and a threaded proximal portion configured to receive a proximal head as disclosed in greater detail above, and/or include filaments in addition to the split portions.

Figure 5A:
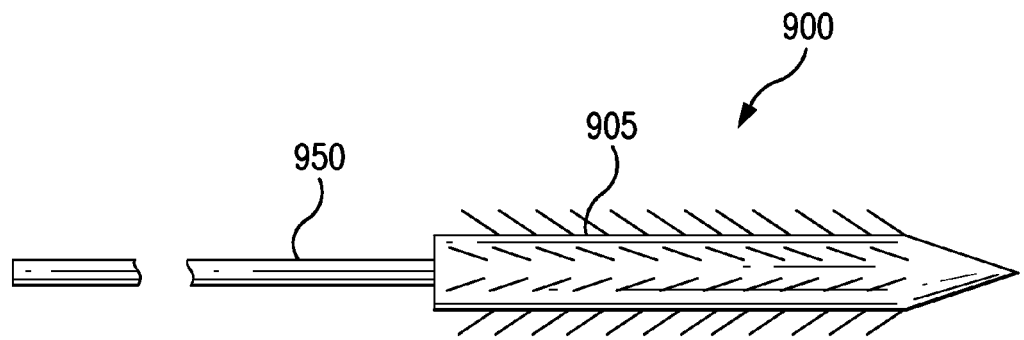
FIG. 5A is an illustration of a surgical implant.
Figure 5B:
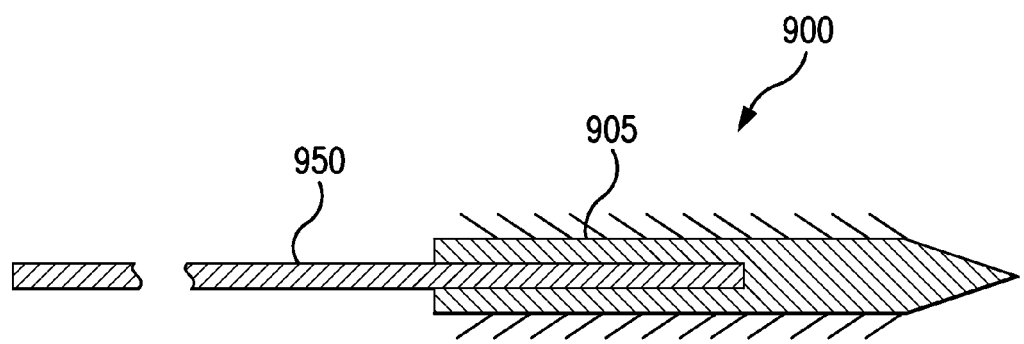
FIG. 5B is a cross-sectional view of the surgical implant of FIG. 5A.

FIGS. 5A and 5B illustrate a surgical micro implant or fastener 900. FIG. 5B is a cross-sectional view of the surgical implant 900 with a cross-sectional plane extending along and including the longitudinal axis of the fastener 900 of FIG. 5A. The fastener 900 includes many feature of the other example fasteners described herein. Further, the fastener includes a filament/suture 950 extending proximally from a proximal end of the fastener body 905. In this regard, when a driver fires the fastener 900, e.g., by application a saline or other precise hydraulic force or any other appropriate mechanism, the depth to which the fastener 900 is driven is limited by the amount of slack in the suture 950. This may be accomplished by fixing a proximal end and/or other proximal portion of the suture 950 to a structure, e.g., a fixed position within the driver device, with a predetermined length and/or slack between the fixing location and the fastener body 905.

Referring to the cross-sectional view of FIG. 5B, the suture 950 may extend longitudinally into an interior location of the fastener head 905. An example manufacturing method may include molding, coextruding, or otherwise forming the fastener head 905 over the suture 950. Coextrusion may be particularly advantageous. It should be appreciated however, that any appropriate manufacturing method may be employed. Further, although a suture 950 of non-stretchable material is provided, it should be understood that other materials, e.g., stretchable materials, may be provided. However, it may be preferable that, even if stretchable, the material have a predeterminable extension limit for particular driving momentums and/or applications. Further, a braided, non-braided, mono-filament, and/or multi-filament material may be provided.

Although the fastener 900 includes micro filaments to anchor into a tissue and resist proximal dislocation after implantation, it should be understood that any other anchoring mechanism, e.g., wings or split portions as described above, may be provided. Moreover, any of the features disclosed with regard to the other example fasteners disclosed herein may be provided in conjunction with the fastener 900.

Figure 6C:
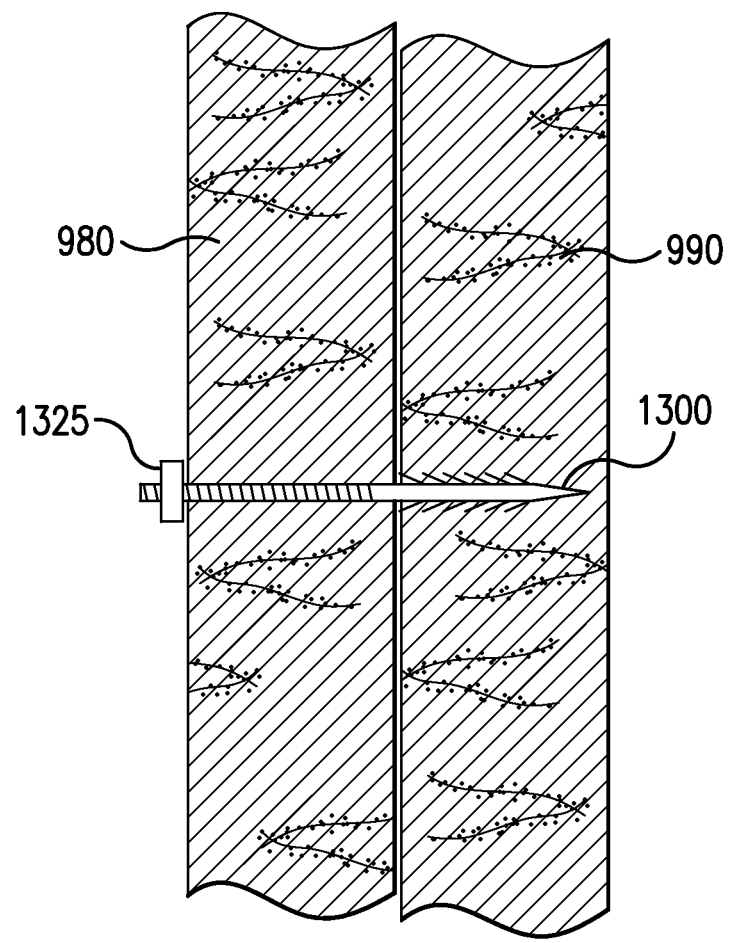

FIGS. 6A to 6C schematically and sequentially illustrate the bringing into apposition of two tissues using a surgical implant 1300, which shares many features in common with the other implants described herein. Implant 1300 has a distal anchoring portion with micro filaments and a proximal threaded portion configured to mate with an internally threaded head 1325, analogous to the implant 200 described above. Implant 1300 also includes a proximally extending filament/suture 1350, analogous to the implant 900 described above.

Referring to FIGS. 6A and 6B, a surgical system 1200 includes a handpiece 1202 configured to drive the fastener 1300 to a predetermined depth. The depth is limited, e.g., by a predetermined amount of slack in the suture 1350. The proximal end of the suture 1350 is attached to a capstan 1205 configured to adjust the length of the suture 1350 extending from capstan 1205. In this regard, the capstan 1205, which may be actuated by a motor system or any other appropriate mechanism, may set the slack by reeling off a predetermined length of suture 1350 prior to driving the fastener 1300 and/or the capstan 1205 may have a predetermined amount of allowed rotation such that driving of the fastener 1300 causes the capstan 1205 to rotate only the predetermined amount, thereby setting the driving depth of the fastener 1300. The determination of the depth and/or the driving velocity of the fastener 1300 may be determined in a processor 1210 of the handpiece 1202. Although the processing takes place in a processor 1210 located in the handpiece 1202, it should be understood that the processor may be disposed in other parts of the device, e.g., in the shaft 1215 and/or the processing may take place at a location separate from the handpiece 1202 and shaft 1215, e.g., at a remote computing unit that communications, e.g., wirelessly, with the surgical device. Further, it should be understood that the capstan 1210 may be disposed in the shaft 1215.

Using any appropriate location determining mechanism, e.g., an imaging mechanism such as a fluoroscopy or ultrasound imaging unit, which may be located in the handpiece 1202, shaft 1215 and/or an external device, the system 1200 determines the location of the first layer of tissue 980 and the second layer of tissue 990. Depending on the application, it may be sufficient for the system 1200 to determine just the respective locations of the tissues 980 and 990. The location may be an approximate location of the center of the tissue or a face, e.g., a proximal face, of each tissue. In the illustrated example, the system determines, e.g., via the imaging device and/or the processor 1210, the respective positions of a first or proximal face 981 of the first tissue 980, a second or distal face 982 of the first tissue 980, a first or proximal face 991 of the second tissue 990, and a second or distal face 992 of the second tissue 990 taken along the line or approximately along the line that the fastener 1300 is to be driven. Based on these positional values, the processor 1210 may determine the thickness of each tissue 980, 990 and the space between the distal face 982 of the first tissue 980 and the proximal face 991 of the second tissue, in addition to the location of each of the distal and proximal faces. Based on the these values, or a portion thereof, the system 1200, e.g., via processor 1210, calculates a precise distance and velocity to drive the fastener. The system 1200 may also take into account the features of the particular fastener being driven (e.g., dimensions, mass, and/or coefficient of friction) and/or the hardness and/or density of the tissue, which may be approximated, e.g., where the tissue is of a known or expected density and/or hardness, or determined based on the imaging data, e.g., fluoroscopy data. The velocity and/or distance may optionally be facilitated by incorporating empirical data into the algorithm or purely based. The depth is controlled, e.g., by precisely controlling the length of suture 1350 via the capstan 1215. The velocity is precisely controlled, e.g., by a hydraulic driver, e.g., a saline driver.

Where the shaft 1215 abuts the first or proximal face 981 of the tissue 980, position of the first or proximal face 981 of the tissue 980 may be determined without using imaging.

As illustrated in FIG. 6A, after the shaft 1215 is placed adjacent the proximal face 981 of the first tissue 980 and the precise driving velocity and depth/position are determined, e.g., by processor 1210 in the handpiece 1205, the system 1200 drives the fastener 1300 in the proximal direction indicated by arrow 1250 through the first tissue 980 across any gap between the first and second tissues 980 and 990, and into the second tissue 990, where the fastener 1300 anchors against distal retraction from the second tissue 990.

Referring to FIG. 6B, the capstan 1210 is then actuated, e.g., by a motor system controlled by, e.g., processor 1210, to proximally reel the suture 1350, thereby drawing the fastener 1300, along with the tissue 990 to which it is anchored, proximally toward the shaft 1215 and the first tissue 980 adjacent the shaft 1215. The proximal direction of movement is indicated by arrow 1260 in FIG. 6B. The first tissue 980 is restrained from proximal movement by, e.g., contact with the distal end of the shaft 1215.

As also illustrated in FIG. 6B the proximal head, or threaded nut, 1325 is moved distally, e.g., by a rotatable driver. The distal direction of movement is illustrated by arrow 1250 in FIG. 6B. The proximal head 1325 may be moved distally at any point after the anchoring fastener 1300 is driven from the shaft 1215. Once the fastener is pulled a sufficient proximal distance, the threaded proximal portion of the body of the fastener 1300 protrudes through the proximal face 981 of the first tissue 980. The proximal head 1325 is then coupled to the threaded portion to form a threaded connection. A rotatable driver then rotates the head 1325 to distally drive the head 1325 to its implanted position, illustrated in FIG. 6C. It should be understood than any final portion of the gap between the distal face 982 of the first tissue and the proximal face 991 of the second tissue 990 may be taken up by continuing to reel in the suture 1350 and/or driving the proximal head 1325 in the distal direction along the threads of the body of the fastener 1300.

After the proximal head 1325 has been fully driven on the threaded shaft of the fastener 1300, the suture 1350, or a portion thereof, may be separated from the fastener 1300, e.g., by cutting. In this regard, the system 1200 may include a cutter or other trimming device, e.g., at the distal end of the shaft 1215, in order to cut the suture 1350. In applications where there is an undesired excess length of externally threaded shaft of the fastener 1300 extending proximally from the fully driven proximal head 1325, the system 1200 may provide for trimming some or all of the excess. In this regard, the system may include a cutter or other trimming device, e.g., at the distal end of the shaft 1215, which may be the same or different than the cutter for the suture 1350, in order to remove some or all of the excess.

Further although two tissues 980 and 990 are illustrated in FIGS. 6A to 6C, it should be understood that the fastener may be driven through any desired number of tissue layers before reaching its anchored position. Moreover, any other example fasteners described herein may be formed with a suture and used in analogous manner to the fastener 1300.

During the procedure illustrated in FIGS. 6A to 6C, the system 1200 may hydraulically drive the implant 1300 or use any other appropriate driving mechanism. Regarding hydraulic delivery, it is noted that a very precise force may be delivered at the distal end portion of the shaft 1215 to drive the fastener 1300. This force may be controlled by the processor 1210 in connection with hydraulics, e.g., in the handpiece. For example, the hydraulic fluid, e.g., saline, may be disposed in a tube extending along the shaft 1215. hydraulics and controls in the handpiece 1202 may then transmit a very precise force, via the hydraulic fluid extending along the shaft 1215, to the distal end portion of the shaft 1215 to precisely drive the fastener 1300.

Figure 7:
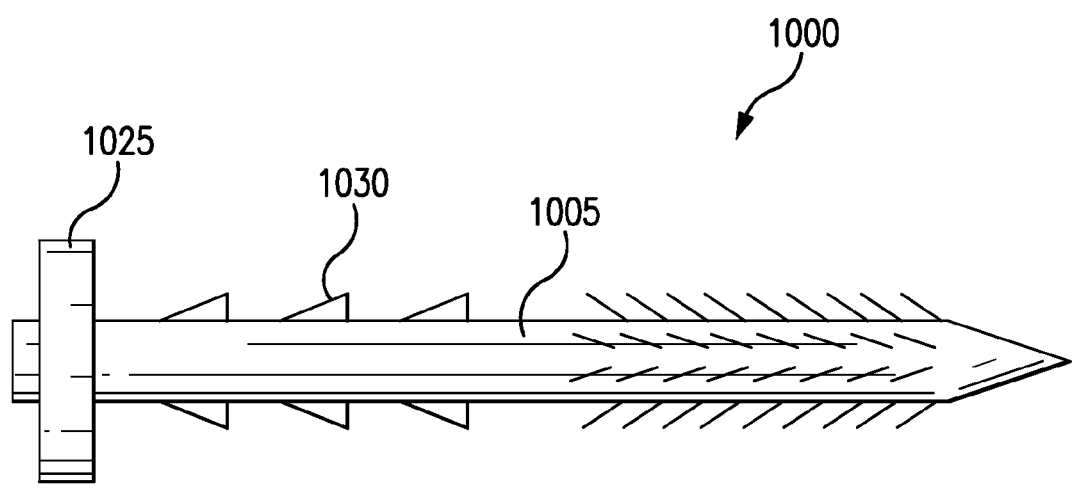
FIG. 7 is an illustration of a surgical implant.

FIG. 7 is an illustration of a surgical implant 1000. The fastener 1000 includes many feature of the other example fasteners described herein. Further, the fastener 1000 includes a proximal portion having a ratcheting mechanism including a micro ratcheting head 1025 and ratchet teeth 1030. The ratcheting mechanism of the implant 1000 performs a function analogous to that of the micro threaded arrangement of the fastener 200 described above. However, as opposed to rotation of the head 225 about the threads 230 of the fastener 200, the ratcheting head 1025 slides, e.g., linearly, along the fastener body 1005. As each ratchet tooth 1030 or circumferential set of ratchet teeth 1030 is distally traversed, the proximal retraction of the head 1025 is resisted or prevented by the ratcheting engagement of a proximal surface of the head 1025 with a distal surface of the ratcheting tooth or teeth 1030. In this regard, for each axial ratcheting position of the head 1025, the fastener body 1005 may have any appropriate number of ratcheting teeth 1030, including a single ratcheting tooth 1030, arranged to engage the ratcheting head 1025. Further, a single tooth 1030 may extend continuously around the entire radial periphery of the fastener body 1005.

Although the fastener 1000 includes micro filaments to anchor into a tissue and resist proximal dislocation after implantation, it should be understood that any other anchoring mechanism, e.g., wings or split portions as described above, may be provided. Moreover, any of the features disclosed with regard to the other example fasteners disclosed herein may be provided in conjunction with the fastener 1000.

Figure 8:
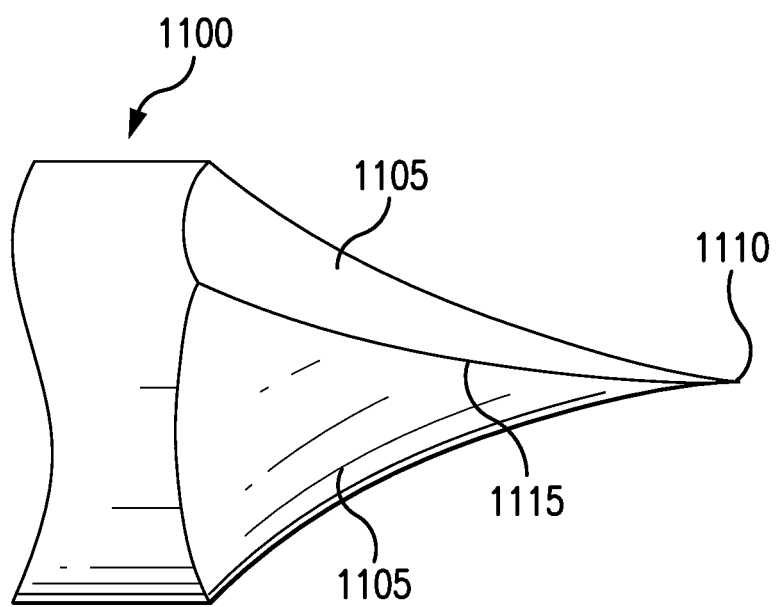
FIG. 8 is an illustration of a distal end portion of a surgical implant.

FIG. 8 is an illustration of a distal end portion of a surgical implant 1100. This distal arrangement may be provided on the distal end of any example fastener disclosed herein. The distal arrangement includes three concave surfaces 1105 that distally converge to form a sharp point 1110. Separating the three concave surfaces 1105 are three tapered cutting edges 1115. These tapered cutting edges 1115 may facilitate penetration of tissue, e.g., soft tissue. Although the end portion illustrated in FIG. 8 includes three concave surfaces 1105 and separated by three corresponding tapered cutting edges 1115, it should be understood that any appropriated number of concave surfaces 1105 and corresponding cutting edges 1115 may be provided.

The various mechanisms described herein provide for a tissue repair system that allows great flexibility. For example, smaller defects may be repairable with a single fastener (e.g., fastener 100 or any other fastener described herein), and larger defects may be repairable with a plurality of fasteners, with or without a washer or plate 2200, as described above. Larger defects, e.g., hernias or large holes, may be more suited for a mesh 1300 application, as described above.

The various implants described herein, e.g., fasteners or anchors 100, 200, 300, 500, and 700 and/or nuts 225, may be formed by molding, e.g., injection molding.

Further, any of the implantable elements described herein, e.g., fasteners 100, 200, 300, 500, and 700 and/or nuts 225, and/or sutures, may be formed wholly or partly of a material absorbable into the patient's body, or of a non-absorbable material, depending on, e.g., the specific application. For example, these elements may be formed of polyglycolic acid (PGA), or a PGA copolymer. These elements may also, or alternatively, be formed of copolymers of polyester and/or nylon and/or other polymer(s). Moreover, these elements may contain one or more shape-memory alloys, e.g., nitinol and/or spring-loaded steel.

Absorbable materials may be advantageous where there is a potential for misfiring or improper locating of the various implants. For example, in a situation where a fastening arm 1100 drives a fastener at an unintended location, or where the tissue does not properly receive the implant, the fastener, e.g., fastener 100, even where not needed, would relatively harmless, as it would eventually absorb into the patient's body.

Although the present invention has been described with reference to particular examples and exemplary embodiments, it should be understood that the foregoing description is in no manner limiting. Moreover, the features described herein may be used in any combination.

What is claimed is:

1. A surgical device, comprising:
 a fastener including a proximal head having a locking mechanism, an elongated body having proximally directed anchoring filaments and a corresponding locking mechanism configured to interlock with the locking mechanism, and a distal tip;
 a filament secured to the fastener and extending proximally from a proximal end of the elongated body;
 a single device body;
 a fastener driver coupled to the single device body and configured to drive the fastener with sufficient impulse through a first unsupported soft tissue or prosthesis and into a second unsupported soft tissue, anchoring the fastener within the second soft tissue; and
 a retraction mechanism coupled to the single device body and configured to proximally reel the filament after the fastener has been driven by the fastener driver of the single device body such that the second unsupported soft tissue is drawn towards the first unsupported soft tissue or prosthesis, the retraction mechanism being configured to apply a sufficient retraction force utilizing the proximal head to the fastener to bring the elongated body into the proximal head thereby engaging the locking mechanism of the proximal head to the corresponding locking mechanism of the elongated body and bringing a proximal surface of the second unsupported soft tissue in direct apposition to a distal surface of the first unsupported soft tissue or prosthesis.

2. The surgical device of claim 1, wherein the fastener driver is configured to drive the fastener at a predetermined distance and velocity based on a determined distance between the first tissue or prosthesis and the second tissue.

3. The surgical device of claim 2, wherein the fastener driver is adjustable to drive the fastener at different distances and velocities based on the determined distances between the first tissue or prosthesis and the second tissue.

4. The surgical device of claim 1, wherein the fastener driver is configured to impart a momentum to the fastener sufficient to drive the fastener through the first soft tissue or prosthesis and into the second soft tissue.

5. The surgical device of claim 4, wherein the fastener driver is configured to transfer hydraulic force to the fastener to impart the momentum.

6. The surgical device of claim 5, wherein saline is provided for hydraulic propulsion.

7. The surgical device of claim 1, wherein the anchoring filaments of the fastener are configured to resist proximal movement of the fastener when the fastener is driven through the first soft tissue or prosthesis and into the second soft tissue.

8. The surgical device of claim 1, wherein the fastener driver includes a plurality of flanges configured to contact a distal face of the proximal head to limit the depth to which the fastener is driven by the fastener driver.

9. The surgical device of claim 8, wherein the flanges are radially expandable from each other to release the proximal head of the fastener.

10. The surgical device of claim 1, wherein the filament is a suture attached to the fastener.

11. A surgical device, comprising:
 a fastener including a proximal end, a proximal head having a locking mechanism, an elongated body having a corresponding locking mechanism configured to interlock with the locking mechanism, and a distal tip;
 a filament secured to the fastener and extending proximally from a proximal end of the elongated body; and
 a fastener driver coupled to a single device body and configured to distally drive the fastener with sufficient impulse through a first unsupported soft tissue or prosthesis and into a second unsupported soft tissue such that the fastener anchors within the second unsupported soft tissue; and
 a retraction mechanism coupled to the single device body and configured to proximally reel the filament after the fastener has been driven by the fastener driver of the single device body such that the second unsupported soft tissue is drawn towards the first unsupported soft tissue or prosthesis, the retraction mechanism being configured to apply a sufficient retraction force utilizing the proximal head to the fastener to bring the elongated body into the proximal head thereby engaging the locking mechanism of the proximal head to the corresponding locking mechanism of the elongated body and bringing a proximal surface of the second unsupported soft tissue in direct apposition to a distal surface of the first unsupported soft tissue or prosthesis.

12. The device of claim 11, wherein the filament is a braided filament.

13. The surgical device of claim 11, wherein the distance to which the fastener is driven is limited by a predetermined amount of slack in the filament prior to the driving, the distance being limited by the tautening of the filament.

14. The device of claim 11, wherein the fastener includes proximally extending anchoring filaments configured to anchor the fastener into the second tissue.

15. The surgical device of claim 11, the fastener driver being configured to impart a momentum to the fastener sufficient to drive the fastener through the first soft tissue and into the second soft tissue when the second soft tissue is unsupported.

16. The surgical device of claim 11, wherein the fastener driver is configured to drive the fastener at a predetermined distance and velocity based on a determined distance between the first tissue or prosthesis and the second tissue.

17. The surgical device of claim 16, wherein the fastener driver is adjustable to drive the fastener at different distances and velocities based on the determined distances between the first tissue or prosthesis and the second tissue.

18. The surgical device of claim 11, wherein the fastener driver is configured to drive the fastener using a hydraulic propulsion.

19. The surgical device of claim 18, wherein saline is provided for the hydraulic propulsion.

20. The surgical device of claim 11, wherein the retraction mechanism comprises a capstan configured to proximally reel the filament after the fastener has been driven by the fastener driver.

21. The surgical device of claim 20, wherein the proximal reeling of the filament causes a corresponding proximal movement of the second tissue when the fastener is anchored in the second tissue.

22. The surgical device of claim 11 wherein the fastener is molded to the filament.

23. The surgical device of claim 22, wherein the fastener is coextruded with the filament.

24. The surgical device of claim 23, wherein the filament is a braided filament.

25. The surgical device of claim 11, wherein the fastener includes a plurality of molded radially disposed anchoring filaments.

26. The surgical device of claim 11, wherein the retraction mechanism comprises a capstan configured to proximally reel the filament after the fastener has been driven by the fastener driver such that the second tissue is drawn to the first tissue or prosthesis.

27. The surgical device of claim 11, wherein the fastener further includes:
   a proximal threaded portion;
   wherein the proximal head is internally threaded and configured to mate with the threaded portion of the fastener.

28. The surgical device of claim 27, wherein the retraction mechanism comprises a capstan configured to proximally reel the filament after the fastener has been driven by the fastener driver such that the second tissue is drawn towards the first tissue or prosthesis.

29. The surgical device of claim 28, wherein the proximal head is coupled to the threaded portion of the fastener such that any remaining gap between the second tissue and the first tissue or prosthesis is closed.

* * * * *